(12) United States Patent
Clarida et al.

(10) Patent No.: US 12,171,496 B2
(45) Date of Patent: Dec. 24, 2024

(54) USING INFRARED TO DETECT PROPER EYE ALIGNMENT BEFORE CAPTURING RETINAL IMAGES

(71) Applicant: Digital Diagnostics Inc., Coralville, IA (US)

(72) Inventors: Warren James Clarida, Iowa City, IA (US); Ryan Earl Rohret Amelon, North Liberty, IA (US); Abhay Shah, Burlington, IA (US); Jacob Patrick Suther, Solon, IA (US); Meindert Niemeijer, Coralville, IA (US); Michael David Abramoff, University Heights, IA (US)

(73) Assignee: Digital Diagnostics Inc., Coralville, IA (US)

( * ) Notice: Subject to any disclaimer, the term of this patent is extended or adjusted under 35 U.S.C. 154(b) by 336 days.

(21) Appl. No.: 16/997,843

(22) Filed: Aug. 19, 2020

(65) Prior Publication Data
US 2022/0054006 A1    Feb. 24, 2022

(51) Int. Cl.
| | |
|---|---|
| *A61B 3/00* | (2006.01) |
| *A61B 3/02* | (2006.01) |
| *A61B 3/10* | (2006.01) |
| *A61B 3/113* | (2006.01) |
| *A61B 3/12* | (2006.01) |

(Continued)

(52) U.S. Cl.
CPC .............. *A61B 3/152* (2013.01); *A61B 3/113* (2013.01); *G16H 40/63* (2018.01)

(58) Field of Classification Search
CPC ......... A61B 3/02; A61B 3/102; A61B 3/1225; A61B 3/0075; A61B 3/113; A61B 3/1015; A61B 3/024

USPC ........ 351/206, 200, 205, 208–210, 221–223, 351/246
See application file for complete search history.

(56) References Cited

U.S. PATENT DOCUMENTS

| | | |
|---|---|---|
| 10,115,194 B2 | 10/2018 | Niemeijer et al. |
| 10,413,180 B1 | 9/2019 | Barriga et al. |
| 11,145,631 B1 * | 10/2021 | Ouderkirk ............... H01L 33/62 |

(Continued)

FOREIGN PATENT DOCUMENTS

| | | | |
|---|---|---|---|
| JP | 3790680 B2 * | 6/2006 | ......... G06K 9/00805 |
| WO | WO 2020/112757 A1 | 6/2020 | |
| WO | WO 2021/029231 A1 | 2/2021 | |

OTHER PUBLICATIONS

PCT International Search Report and Written Opinion, PCT Application No. PCT/US2021/045727, Nov. 29, 2021, 18 pages.

(Continued)

*Primary Examiner* — Dawayne Pinkney
(74) *Attorney, Agent, or Firm* — Fenwick & West LLP

(57) ABSTRACT

Systems and methods are disclosed herein for detecting eye alignment during retinal imaging. In an embodiment, the system receives an infrared stream from an imaging device, the infrared stream showing characteristics of an eye of a patient. The system determines, based on the infrared stream, that the eye is improperly aligned at a first time, and outputs sensory feedback indicative of the improper alignment. The system detects, based on the infrared stream at a second time later than the first time, that the eye is properly aligned, and receives an image of a retina of the properly aligned eye from the imaging device.

20 Claims, 5 Drawing Sheets

(51) Int. Cl.
*A61B 3/15* (2006.01)
*G16H 40/63* (2018.01)

(56) References Cited

U.S. PATENT DOCUMENTS

| | | | |
|---|---|---|---|
| 2016/0302665 A1 | 10/2016 | Swedish et al. | |
| 2016/0341961 A1* | 11/2016 | Mullins | G02B 27/017 |
| 2017/0278241 A1* | 9/2017 | Abramoff | G06T 7/0002 |
| 2018/0064337 A1 | 3/2018 | Abramoff et al. | |
| 2019/0028634 A1 | 1/2019 | Koehler et al. | |
| 2019/0082958 A1 | 3/2019 | Keshishian | |
| 2019/0303723 A1* | 10/2019 | Linden | G06T 7/70 |
| 2020/0257879 A1 | 8/2020 | Solanki et al. | |
| 2021/0290055 A1* | 9/2021 | Clarida | A61B 3/0025 |

OTHER PUBLICATIONS

European Patent Office, Extended European Search Report and Written Opinion, European Patent Application No. 21858855.6, Jun. 17, 2024, 10 pages.

\* cited by examiner

USING INFRARED TO DETECT PROPER EYE ALIGNMENT BEFORE CAPTURING RETINAL IMAGES

BACKGROUND

This invention relates generally to autonomous diagnosis of retinal abnormalities, and more specifically to using spectral waves, such as infrared, to detect proper eye alignment when capturing retinal images.

Historically, to test for abnormalities in a patient's eye, medical professionals have personally operated imaging devices to capture retinal images. Medical professionals are trained to guide a camera and ensure that it is properly aligned with a patient's pupil when capturing retinal images. Autonomous systems are being developed for diagnosing retinal abnormalities, and are designed to capture images of a patient's retina (interchangeably used with the word fundus herein) and analyze those images for abnormalities without a need for a medical professional to analyze the image. But without a medical professional operating an imaging device, imaging devices are incapable of ensuring that a patient's eye is properly aligned, and thus these autonomous systems are prone to error. For example, while a guiding light may be illuminated in the imaging device, and a patient may be instructed (e.g., by an operator who is not a medical professional) to focus on the guiding light to align the patient's pupil with a camera lens, the patient may fail to do so, and an image will nonetheless be captured that is insufficient for an abnormality analysis.

SUMMARY

Systems and methods are provided herein for detecting eye alignment during retinal imaging. For example, during an eye examination, a patient may place his eyes in the field of view of an imaging device that is configured to capture retinal images. Rather than have a medical professional operate the imaging device to instruct a patient to align the patient's eyes properly with the camera, the imaging device here may be configured to determine proper alignment without operation by a medical professional. For example, infrared imaging of the patient's eye may be performed to determine eye alignment, and instructions may be output (e.g., voice commands) to aid the patient in adjusting the patient's eye positioning to properly align the eye. In this manner, fewer flashes need to be taken to capture images of the patient's eye for retinal disease diagnosis, thus preventing the need to expose a patient's eyes unnecessarily to multiple flashes due to unsuccessful imaging.

To these ends and others, in an embodiment, a processor (e.g., of a server) receives an infrared stream from an imaging device, the infrared stream showing characteristics of an eye of a patient. The processor determines, based on the infrared stream, that the eye is improperly aligned at a first time, and outputs sensory feedback indicative of the improper alignment. The processor then detects, based on the infrared stream at a second time later than the first time, that the eye is properly aligned, and receives an image of a retina of the properly aligned eye from the imaging device.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION (a) Environment Overview

Figure 1:
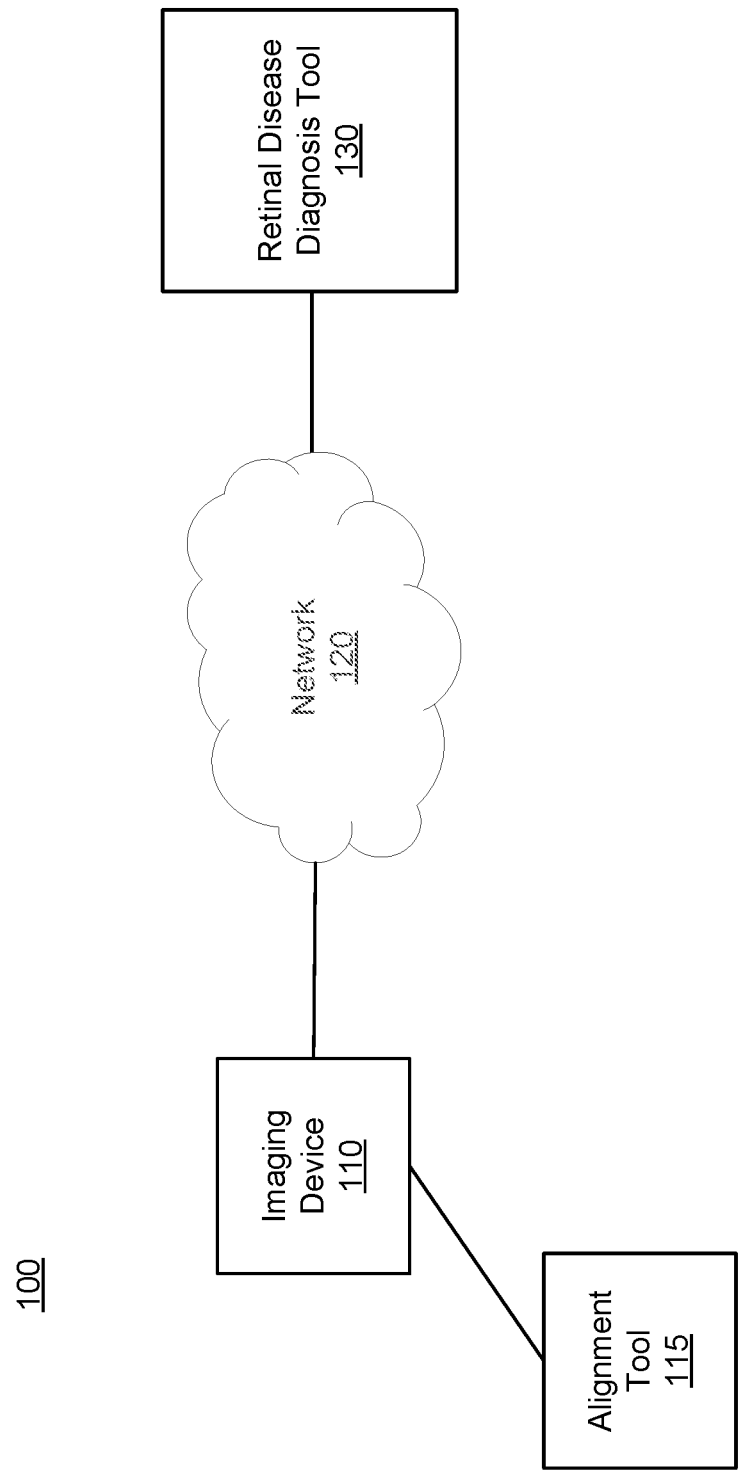
FIG. 1 is an exemplary block diagram of system components in an environment for utilizing an alignment tool, in accordance with one embodiment.

FIG. 1 is an exemplary block diagram of system components in an environment for utilizing an alignment tool, in accordance with one embodiment. Environment 100 includes imaging device 110, alignment tool 115, network 120, and retinal disease diagnosis tool 130. Imaging device 110 is a device configured to capture one or more images of a retina of a patient's eye. Imaging device 110 may be caused to capture such images through manual operation, autonomously as instructed by computer program instructions or external signals (e.g., received from alignment tool 115), or a combination thereof. Examples of what these images may look like, and how they are derived, are described in commonly-owned U.S. patent application Ser. No. 15/466,636, filed Mar. 22, 2017, the disclosure of which is hereby incorporated by reference herein in its entirety.

Alignment tool 115 is operably coupled to imaging device 110, and may verify that an eye of a patient is properly aligned. Responsive to verifying that the eye of the patient is properly aligned, alignment tool 115 may instruct imaging device 110 to capture an image. Alignment tool 115 may use images or a stream of images from various spectra, such as infrared images, to determine whether the eye of the patient is properly aligned. While depicted as a standalone entity, this is for illustrative purposes only; alignment tool 115 may alternatively sit on-board imaging device 110 (e.g., having been installed as a module), or may be implemented as part of retinal disease diagnosis tool 130, acting on information received over network 120. Further details about the functionality of alignment tool 115 are described in further detail below with respect to FIGS. 3-5.

After capturing an image (e.g., based on an instruction from alignment tool 115), imaging device 110 (or alternatively, alignment tool 115) transmits the image to retinal disease diagnosis tool 130 for processing. Retinal disease diagnosis tool 130 autonomously analyzes received retinal images and determines, using machine learning analysis of biomarkers therein, a diagnosis. The diagnosis may specifically be a determination that the user has a particular disease, such as diabetic retinopathy, or may be a determination that the user likely has a disease and should thus see a doctor for confirmation and treatment. The manners in which retinal disease diagnosis tool 140 performs the analysis and determines a diagnosis are further discussed in commonly-owned U.S. Pat. No. 10,115,194, the disclosure of which is hereby incorporated by reference herein in its entirety. While depicted as a separate entity from realignment tool 115, retinal disease diagnosis tool 130 may be instantiated on a same device or set of devices as alignment tool 130, and may be, in part or in full, installed as a module on imaging device 110, similar to the manner in which alignment tool 130 may be installed as a module in imaging device 110. Though not depicted in FIG. 1, one or more additional imaging devices may be used to capture an external image including some or all of a patient (e.g., the patient's skin or hair). Any retinal diagnosis performed by retinal diagnosis tool 130 may utilize such external images.

(b) Exemplary Imaging Device Components

Figure 2:
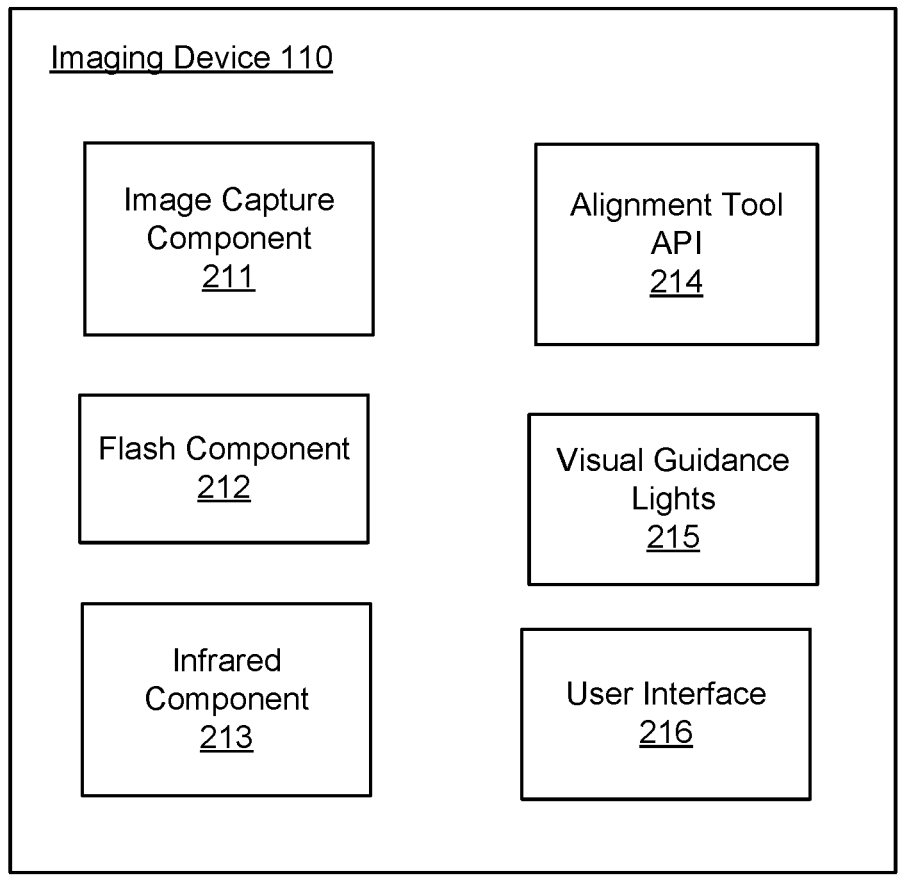
FIG. 2 is an exemplary block diagram of modules and components of an imaging device, in accordance with one embodiment.

FIG. 2 is an exemplary block diagram of modules and components of an imaging device, in accordance with one embodiment. Imaging device 110 includes image capture component 211, flash component 212, infrared component 213, alignment tool application protocol interface (API) 214, visual guidance lights 215, and user interface 216. While not depicted, imaging device 110 may include other components, such as on-board instantiations of either or both of alignment tool 115 and retinal disease diagnosis tool 130, and any components thereof. Imaging device 110 may include any databases or memory for performing any functions described herein. Imaging device 110 may exclude some depicted components as well. For example, imaging device may exclude visual guidance lights 215.

Image capture component 211 may be any sensor configured to capture an image of a patient's retina. For example, a specialized lens may be used to capture the image of the patient's retina. Flash component 212 may be any component capable of illuminating a patient's retina during the image capture by image capture component 211, and may be configured to emit light in concert with an image capture operation of image capture component 211. Image capture component 211 may also be configured with an external image capture component 211 for capturing an image including a patient's skin and/or hair.

Infrared component 213 is an infrared sensor that is configured to transmit infrared radiation to a patient's retina and determine absorption thereof. Infrared component 213 may generate a heat map showing absorption of the infrared transmission across the patient's retina. Infrared component 213 transmits the absorption determination and/or heat map to a processor (e.g., of alignment tool 130) for processing with respect to determination of eye alignment of the patient. Infrared component 213 may stream images that it captures and/or absorption maps or other post-processed renderings of infrared images (hereafter collectively referred to as infrared images) to alignment tool 115. The term stream, as used herein, may refer to some or all transmitting infrared images as, or soon after, they are captured by infrared component 213.

Alignment tool API 214 interfaces with alignment tool 130 to translate commands from alignment tool 130 to imaging device 110. Exemplary commands may include a command to capture an image, a command to adjust an intensity of light emitted by flash component 212, a command to activate visual guidance lights 215, and the like. These commands and how they are generated are discussed in further detail with reference to FIG. 3 below. Alignment tool API 214 is also used by imaging device 110 to transmit infrared images to alignment tool 115.

Visual guidance lights 215 may include one or more lights within the periphery of a patient using imaging device 110 that may be selectively activated. A guiding light may activate that is designed to capture the attention of the patient, who is instructed to gaze at the guiding light (e.g., in order to align the pupil with a lens for capture of a retinal image). Visual guidance lights may include arrows in any direction (e.g., left, right, up, down, or diagonally in any direction), where the arrows are lit up by lighting certain pixels or lights (e.g., LEDs) in a grid of pixels or lights. The arrows may indicate a direction to which the patient's gaze should shift in order to improve alignment. Further details about visual guidance lights 215 and their functionality will be described with reference to visual feedback module 340, which may generate instructions for selectively activating one or more of the visual guidance lights 215.

User interface 216 is an interface with which a user (e.g., operator or patient) of imaging device 110 may command imaging device 110 to perform any function it is capable of performing, such as capturing images, adjusting flash intensity, capturing infrared information, and the like. User interface 216 may also output information to the user (e.g., audio or visual information). User interface 216 may be any hardware or software interface, and may include physical components (e.g., buttons) and/or graphical components (e.g., on a display, such as a touch screen display). User interface 216 may be located on imaging device 110, may be a device peripheral to imaging device 110, or may be located on a device separated from imaging device 110 by network 120, thus enabling remote operation of imaging device 110.

(c) Exemplary Alignment Tool Components

Figure 3:
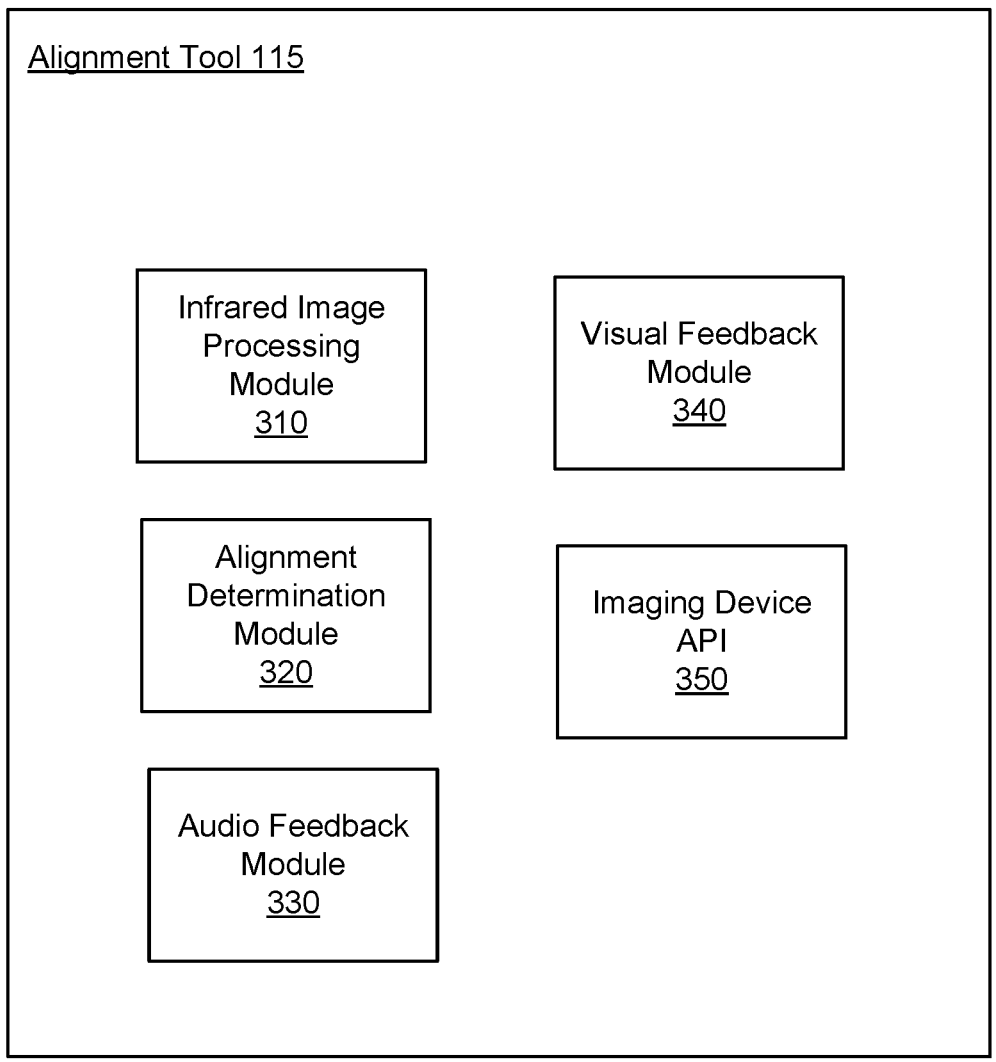
FIG. 3 is an exemplary block diagram of modules and components of an alignment tool, in accordance with one embodiment.

FIG. 3 is an exemplary block diagram of modules and components of an alignment tool, in accordance with one embodiment. Alignment tool 115 includes infrared image processing module 310, alignment determination module 320, audio feedback module 330, visual feedback module 340, and imaging device API 350. While not depicted, alignment tool 115 may include other components such as additional modules, and any databases or memory for performing any functions described herein. Alignment tool 115 may exclude some depicted components as well. For example, alignment tool 130 may exclude visual feedback module 340.

Infrared image processing module 310 receives an infrared stream from imaging device 110. Infrared refers to an exemplary spectrum that may be used in accordance with the embodiments disclosed herein; however, this is non-limiting. Other spectra may be used wherever infrared is described herein, such as ultraviolet, x-ray, and so on. Infrared image processing module 310 may receive the infrared stream by way of imaging device API 350, which interfaces alignment tool 115 with imaging device 110. Infrared image processing module 310 may command imaging device 110 to begin streaming infrared data (e.g., when a new patient is detected as using imaging device 110). Alternatively, infrared image processing module 310 may command imaging device to begin streaming infrared data upon a condition occurring (e.g., imaging device 110 being initialized for capturing a retinal image).

Infrared image processing module 310 may perform processing on the received infrared stream (e.g., to render the data contained therein usable by alignment determination module 320). For example, infrared image processing module 310 may take raw infrared data as input and may generate an infrared heat map or a contour map showing portions of the patient's eye or eyes. As another example, infrared image processing module 310 may generate a vector map showing a change in eye position between one or more frames, thus indicating a direction and distance in which an eye had moved or rotated. This vector map may be used, in addition or separately from, raw or otherwise processed infrared information in determining eye alignment.

Alignment determination module 320 determines whether an eye of a patient is properly aligned for capture of a retinal image. The term properly aligned, as used herein, may refer to an image that satisfies criteria for performing an autonomous diagnosis of whether a patient has retinal disease. Improper alignment generally occurs because a patient's gaze is pointed toward a direction that obscures an object of interest, such as the patient's pupil or the retina. In an embodiment where a patient is instructed to look toward a fixation light, proper alignment occurs when the image is aligned with a landmark of the retina (e.g., the center of the retina). When images are captured, high-intensity flash is used, and guidelines suggest that a limit to how many times a patient is flashed during an appointment should be limited for patient health and safety reasons. Improper alignment causes ineffective images to be captured for autonomous diagnosis, thus requiring additional images to be captured, which requires additional flashing of the patient's eye. Alignment determination module 320 may be used to determine proper alignment before flashing the patient's eye, thus improving patient health and safety.

In an embodiment, alignment determination module 320 may determine whether alignment is proper based on whether, and where, the object of interest (that is, either the pupil of the eye or the retina) is shown in the infrared stream. Alignment determination module 320 may determine that the existence of the object of interest in the infrared stream alone is enough to determine that alignment is proper. Alignment determination module 320 may alternatively, or additionally, require other factors to be true. For example, alignment determination module 320 may require that imaging device 110 be focused to determine that the image is properly aligned. Imaging device 110 may be programmed to auto-focus upon detecting an object of interest, such as the pupil of the eye, or such as the pupil of the eye being in, or within a threshold distance of, the center of the infrared image. Alignment determination module 320 may determine based on the infrared stream, or based on auxiliary information indicating whether or not imaging device 110 is focused, whether imaging device 110 is focused. Responsive to determining that imaging device 110 is focused, alignment determination module 320 may determine that alignment is proper. Absent the object of interest and/or focus of imaging device 110 being present in the infrared stream, alignment determination module 320 may determine that the alignment of the patient's eye is improper.

Alignment determination module 320 may use other means for determining, based on the infrared stream, that alignment is proper. For example, a patient may twitch his or her eye in a given direction based on stimuli, such as the lighting of a guide light, or the aural instruction of an operator or as output from a speaker of alignment tool 115 and/or imaging device 110. Alignment determination module 320 may determine that alignment is proper responsive to detecting a twitch. That is, it is likely that the patient moved their eye to a proper alignment based on the stimuli. Alignment determination module 320 may detect the switch based on a threshold movement of the patient's eye over an interval of time or across a certain, small number of frames. Alignment determination module 320 may detect the switch using the aforementioned vector map, and determining whether movement vectors on the vector map indicate that a twitch has occurred.

Because a twitch might occur due to reasons other than stimuli directly designed to cause a patient to twitch their eye to a particular position, alignment determination module 320 may perform further processing before determining that the eye is properly aligned. In an embodiment, responsive to detecting the twitch, alignment determination module 320 may capture an image. The captured image may be a frame of the infrared stream following the twitch, or may be a visual image commanded to be taken by imaging device 110 and transmitted to alignment determination module 320 for processing.

Alignment determination module 320 may then determine whether the image satisfies a quality parameter. The quality parameter may include determining whether image quality is sufficient. For example, image quality may be poor where the frame is blurred due to continued movement of the eye in the midst of a twitch. Alignment determination module 320 may determine image quality based on one or more metrics, such as blurriness, focus, and so on. The quality parameter may include other features, such as whether a biomarker is detected in the candidate image. For example, alignment determination module 320 may determine, based on either a visual or infrared frame, whether the optic disk, and/or any other biomarker, is detectable in the image. Other example quality parameters may include determining whether an artifact is blocking some or all of the image (e.g., a patient's eyelashes are obscuring the image). Responsive to determining that the candidate image satisfies the quality parameter, alignment determination module 320 may determine that the patient's eye is properly aligned. Responsive to determining that the candidate image does not satisfy the quality parameter, alignment determination module 320 may determine that the patient's eye alignment is improper.

In an embodiment, quality may be determined by inputting the candidate image into a machine learning model, and receiving as output from the machine learning model an indication of whether the candidate image is of sufficient quality. In some embodiments, the machine learning model may be a supervised learning model. In such embodiments, the machine learning model may be trained using a labeled training set of images, where each image in the training set is labeled as to whether the image is, or is not, of sufficient quality. In some embodiments, the machine learning model may be trained using unsupervised techniques.

Where alignment is determined to be improper, feedback may be provided to the patient in order to encourage the patient to adjust the position of the patient's eye such that the eye is properly aligned. In an embodiment, alignment determination module 320 determines a particular adjustment that must be made for the eye to be properly aligned. For example, alignment determination module 320 determines where the pupil is focused using the infrared stream, and determines that the pupil must shift in a particular direction in order to be properly aligned. In another embodiment, alignment determination module 320 is unable to identify the particular adjustment that must be made for the eye to be properly aligned (e.g., because the pupil is not detectable in the infrared stream). Depending on the scenario, audio feedback module 330 and visual feedback module 340 may provide feedback to the patient to make a proper adjustment.

In an embodiment, alignment determination module 320 determines whether the eye is aligned based on output from a machine learning model. For example, alignment determination module 320 may input one or more frames of the infrared stream into a machine learning model, and may receive as output from the machine learning model a probability that the eye is probably aligned and/or an output indicating that the eye is, or is not, properly aligned. Where the outputs are probabilities, alignment determination module 320 may compare the probabilities to a threshold (e.g., over 92% likelihood that the eye is aligned), and may determine, based on the probabilities exceeding the threshold, that the eye is aligned.

The machine learning model may be trained using a labeled data set of infrared frames, the labels indicating that the eye is, or is not, aligned. In an embodiment, the data set may include additional labels, such as labels indicating an offset from proper alignment (e.g., eye would be aligned if rotated three degrees to the right). In such a case, alignment determination module 320 may additionally, or alternatively, output the offset, which may be used by audio feedback module 330 and/or visual feedback module 340 in determining instructions. The machine learning model may be any machine learning model. For example, the machine learning model may be a neural network, such as a convolutional neural network.

In an embodiment, a model, such as a machine learning model and/or a deterministic model may be trained to take infrared frames as input. For example, frames from a beginning of an alignment process until a correct alignment is obtained may be input into the model. The model may also take as input a representation of the instructions provided to the patient (e.g., a voice-to-text transcript where a human operator is providing instructions, or a reading of automated instructions provided to the patient). The model may, based on these inputs, output an indication of whether the provided instructions are being administered correctly by the operator and/or whether the provided instructions are being accurately followed by the patient. The output may be binary (e.g., incorrect or correct administration). The output may indicate a particular error in the instructions (e.g., a particular portion of the instructions were incorrect and should instead be to perform some other action). The output may be a particular new instruction that will fix alignment (e.g., shift eye gaze three degrees to the right). The output may be a set of probabilities corresponding to different corrective activities and/or instructions and/or whether the administration is correct, whereby alignment determination module 320 may determine by comparing the probabilities to respective thresholds what to output to the patient and/or operator. The machine learning model may be a trained region-based convolutional neural network (RCNN) or any other type of machine learning model.

Audio feedback module 330 may output aural instructions to the patient (e.g., using a speaker of imaging device 110 or a peripheral speaker operably coupled to alignment tool 115). The aural instructions may be to shift an eye in any particular direction, such as up, down, left, right, or some combination thereof. In an embodiment where the exact needed adjustment is known to properly align the patient's eye, the instructions may correspond with the needed eye movement. In an embodiment where the exact needed adjustment is not known, the patient may be instructed to move their eye (e.g., "slowly move your eye upward") until the pupil is detected in the infrared stream, at which time alignment determination module 320 may determine the needed adjustment using the aforementioned processes. Audio feedback module 330 may then provide further instructions based on the needed adjustment.

Visual feedback module 340 operates in a similar manner to audio feedback module 330, and may operate in combination with, or separately from, audio feedback module 330 (that is, audio and visual feedback may occur concurrently, or separately). As mentioned in the foregoing, imaging device 110 may include imaging components (e.g., pixels, light-emitting diodes, etc.) that appear in a field of view of a patient when using imaging device 110. In an embodiment, visual feedback module 340 may activate a guide light. The guide light is activated at a position in the patient's field of view, that, if gazed at, would align the patient's eye properly. Alignment tool 115 may have audio feedback module 330 provide instructions to gaze at the guide light when the guide light is activated.

In another embodiment, or where the patient is not responsive to the guide light, visual feedback module 340 may activate imaging components to form an indicator, such as an arrow, in a direction toward which the patient should adjust the patient's gaze. In an embodiment, visual feedback module 340 may activate an imaging component, and audio feedback module 330 may output aural instructions to follow the imaging component with the patient's gaze as the imaging component moves. Visual feedback module 340 may selectively activate and de-activate imaging components to have the light continue to move in the patient's field of view. As the patient moves the patient's gaze to follow the movement of the light, alignment determination module 320 may determine whether alignment is improper and/or whether the pupil can be detected, and may feed back further adjustments needed to obtain a proper alignment (as determined using the processes discussed above) to visual feedback module 340 for further movement of the light.

(d) Exemplary Computing Machine Architecture

Figure 4:
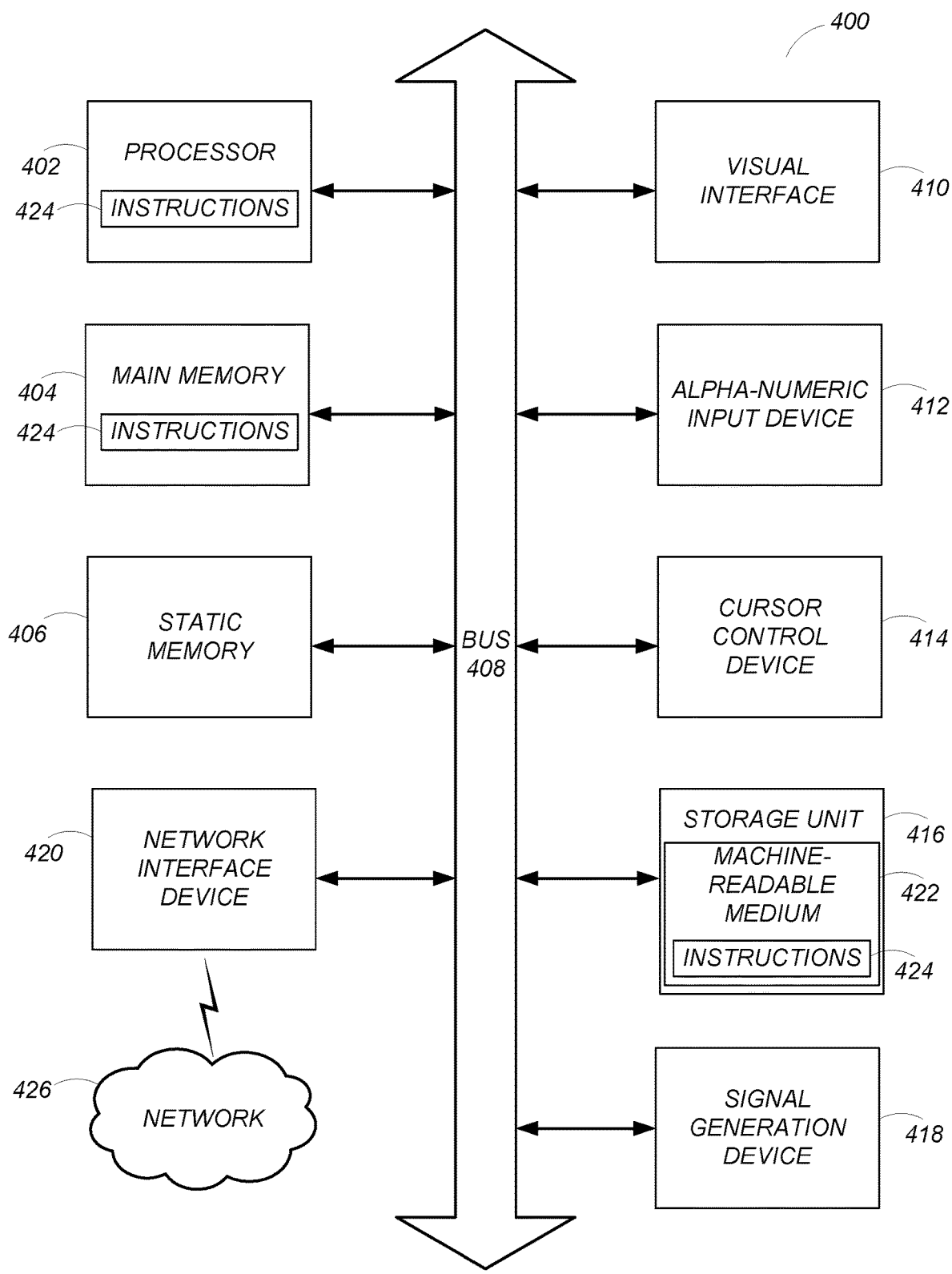
FIG. 4 is a block diagram illustrating components of an example machine able to read instructions from a machine-readable medium and execute them in a processor (or controller).

FIG. 4 is a block diagram illustrating components of an example machine able to read instructions from a machine-readable medium and execute them in a processor (or controller). Specifically, FIG. 4 shows a diagrammatic representation of a machine in the example form of a computer system 400 within which program code (e.g., software) for causing the machine to perform any one or more of the methodologies discussed herein may be executed. The program code may be comprised of instructions 424 executable by one or more processors 402. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 424 (sequential or otherwise) that specify actions to be taken by that machine. Further, while only a single machine is illustrated, the term "machine" shall also be taken to include any collection of machines that individually or jointly execute instructions 124 to perform any one or more of the methodologies discussed herein.

The example computer system 400 includes a processor 402 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 404, and a static memory 406, which are configured to communicate with each other via a bus 408. The computer system 400 may further include visual display interface 410. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 410 may include or may interface with a touch enabled screen. The computer system 400 may also include alphanumeric input device 412 (e.g., a keyboard or touch screen keyboard), a cursor control device 414 (e.g., a mouse, a trackball, a joystick, a motion sensor, or other pointing instrument), a storage unit 416, a signal generation device 418 (e.g., a speaker), and a network interface device 420, which also are configured to communicate via the bus 408.

The storage unit 416 includes a machine-readable medium 422 on which is stored instructions 424 (e.g., software) embodying any one or more of the methodologies or functions described herein. The instructions 424 (e.g., software) may also reside, completely or at least partially, within the main memory 404 or within the processor 402 (e.g., within a processor's cache memory) during execution thereof by the computer system 400, the main memory 404 and the processor 402 also constituting machine-readable media. The instructions 424 (e.g., software) may be transmitted or received over a network 426 via the network interface device 420.

While machine-readable medium 422 is shown in an example embodiment to be a single medium, the term "machine-readable medium" should be taken to include a single medium or multiple media (e.g., a centralized or distributed database, or associated caches and servers) able to store instructions (e.g., instructions 424). The term "machine-readable medium" shall also be taken to include any medium that is capable of storing instructions (e.g., instructions 424) for execution by the machine and that cause the machine to perform any one or more of the methodologies disclosed herein. The term "machine-readable medium" includes, but not be limited to, data repositories in the form of solid-state memories, optical media, and magnetic media.

(e) Exemplary Data Flow for Determining Eye Alignment

Figure 5:
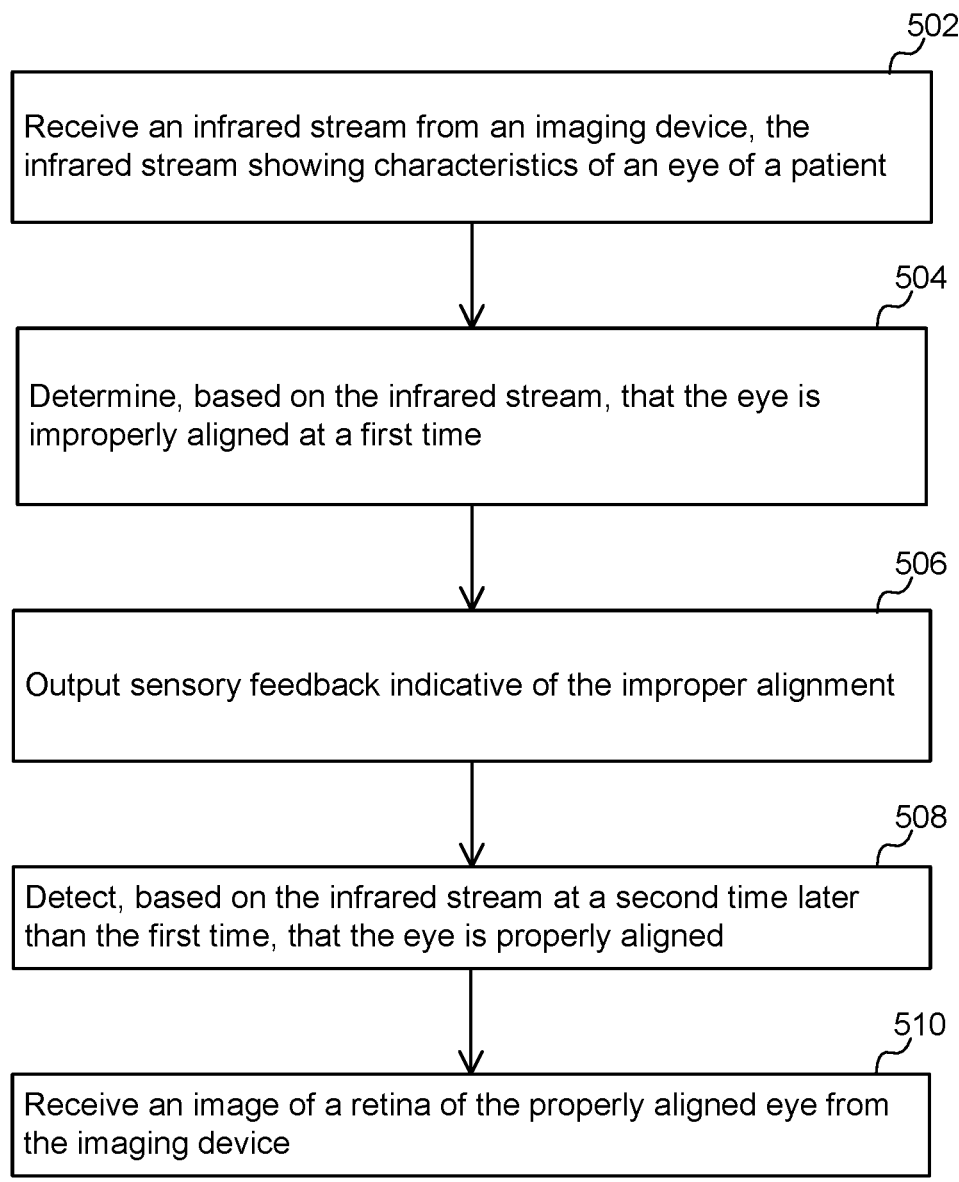
FIG. 5 depicts an exemplary flow chart for detecting eye alignment during retinal imaging, in accordance with one embodiment.

FIG. 5 depicts an exemplary flow chart for detecting eye alignment during retinal imaging, in accordance with one embodiment. Process 500 begins with one or more processors (e.g., processor 402) of a device used to run alignment tool 130 receiving 502 an infrared stream from an imaging device (e.g., using infrared image processing module 310), the infrared stream showing characteristics of an eye of a patient. Alignment tool 130 determines 504, based on the infrared stream, that the eye is improperly aligned at a first time (e.g., using alignment determination module 320). An improper alignment determination may be based on any number of factors, such as the pupil of the patient's eye not being shown in the infrared stream, or that imaging device 110 is not focused. In an embodiment, the alignment determination 504 is made by inputting a frame of the infrared stream into a machine learning model, and receiving as output from the machine learning model information indicating the eye is improperly aligned at a first time Alignment tool 130 outputs 506 sensory feedback indicative of the improper alignment (e.g., using audio feedback module 330 and/or visual feedback module 340). The sensory feedback may be output to an operator (e.g., a layperson who is operating imaging device 110), to a patient, or to both a patient and an operator. Alignment tool 130 detects 508, based on the infrared stream at a second time later than the first time, that the eye is properly aligned (e.g., using alignment determination module 320). A proper alignment determination may be based on detecting a twitch of the patient's eye. Where a twitch forms the basis for a proper alignment determination, an image (e.g., an infrared frame) may be captured and verified against a quality parameter (e.g., image quality, artifact, biomarker detection, etc.) before finalizing the determination that the eye is in fact properly aligned. Alignment tool 130 receives 510 an image of a retina of the properly aligned eye from imaging device 110. Alignment tool 130 may command imaging device 110 to automatically capture and transmit the image of the retina to alignment tool 130 responsive to detecting a proper alignment. Alignment tool 130 may transmit the image to retinal disease diagnosis tool 130 to perform an autonomous diagnosis of the patient's eye.

(f) Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for detecting eye alignment during retinal imaging, the method comprising:
   receiving an infrared stream from an imaging device, the infrared stream showing infrared absorption within a retina of an eye of a patient;
   inputting a frame of the infrared stream into a machine learning model;
   receiving as output from the machine learning model information indicating the eye is improperly aligned at a first time;
   responsive to receiving the output from the machine learning model, outputting sensory feedback indicative of the improper alignment;
   detecting, based on the infrared stream at a second time later than the first time, that the eye is properly aligned using the machine learning model; and
   responsive to detecting that the eye is properly aligned, automatically instructing the capture of an image of the retina of the properly aligned eye from the imaging device and receiving the image.

2. The method of claim 1, wherein the information indicates that the eye is improperly aligned at the first time due to at least one of:
   a pupil of the eye is not shown in the infrared stream; and
   the imaging device is not focused.

3. The method of claim 1, wherein the imaging device is operated autonomously, and wherein the sensory feedback comprises a visual or aural output to the patient with instructions on how to correct the improper alignment.

4. The method of claim 1, wherein the imaging device is operated by an operator other than the patient, and wherein the sensory feedback is provided to the operator.

5. The method of claim 1, further comprising, responsive to detecting that the eye is properly aligned, commanding the imaging device to capture the image.

6. The method of claim 1, wherein detecting that the eye is properly aligned comprises detecting a twitch of the eye.

7. The method of claim 6, wherein detecting that the eye is properly aligned further comprises:
   responsive to detecting the twitch, capturing a candidate image;
   determining whether the candidate image satisfies a quality parameter; and
   responsive to determining that the candidate image satisfies the quality parameter, determining that the eye is properly aligned.

8. The method of claim 7, wherein the quality parameter comprises at least one of image quality in the candidate image and detection of an artifact in the candidate image.

9. The method of claim 1, further comprising autonomously diagnosing a retinal condition of the retina based on features of the image of the retina.

10. A computer program product for detecting eye alignment during retinal imaging, the computer program product comprising a non-transitory computer- readable storage medium containing computer program code for:
    receiving an infrared stream from an imaging device, the infrared stream showing infrared absorption within a retina of an eye of a patient;
    inputting a frame of the infrared stream into a machine learning model;
    receiving as output from the machine learning model information indicating the eye is improperly aligned at a first time;
    responsive to receiving the output from the machine learning model, outputting sensory feedback indicative of the improper alignment;
    detecting, based on the infrared stream at a second time later than the first time, that the eye is properly aligned using the machine learning model; and
    responsive to detecting that the eye is properly aligned, automatically instructing the capture of an image of the retina of the properly aligned eye from the imaging device and receiving the image.

11. The non-transitory computer-readable medium of claim 10, wherein the information indicates that the eye is improperly aligned at the first time due to at least one of:
    a pupil of the eye is not shown in the infrared stream; and
    the imaging device is not focused.

12. The non-transitory computer-readable medium of claim 10, wherein the imaging device is operated autonomously, and wherein the sensory feedback comprises a visual or aural output to the patient with instructions on how to correct the improper alignment.

13. The non-transitory computer-readable medium of claim 10, wherein the imaging device is operated by an operator other than the patient, and wherein the sensory feedback is provided to the operator.

14. The non-transitory computer-readable medium of claim 10, wherein the computer program code is further for, responsive to detecting that the eye is properly aligned, commanding the imaging device to capture the image.

15. The non-transitory computer-readable medium of claim 10, wherein detecting that the eye is properly aligned comprises detecting a twitch of the eye.

16. The non-transitory computer-readable medium of claim 15, wherein detecting that the eye is properly aligned further comprises:
    responsive to detecting the twitch, capturing a candidate image;
    determining whether the candidate image satisfies a quality parameter; and
    responsive to determining that the candidate image satisfies the quality parameter, determining that the eye is properly aligned.

17. The non-transitory computer-readable medium of claim 16, wherein the quality parameter comprises at least one of image quality in the candidate image and detection of an artifact in the candidate image.

18. The non-transitory computer-readable medium of claim 10, wherein the computer program code is further for autonomously diagnosing a retinal condition of the retina based on features of the image of the retina.

19. A computer program product for detecting eye alignment during retinal imaging, the computer program product comprising a computer-readable storage medium containing computer program code that comprises:
    a first module for receiving an infrared stream from an imaging device, the infrared stream showing infrared absorption within a retina of an eye of a patient;
    a second module for inputting a frame of the infrared stream into a machine learning model;
    a third module for receiving as output from the machine learning model information indicating the eye is improperly aligned at a first time;
    a fourth module for, responsive to receiving the output from the machine learning model, outputting sensory feedback indicative of the improper alignment;

a fifth module for detecting, based on the infrared stream at a second time later than the first time, that the eye is properly aligned using the machine learning model; and a sixth module for, responsive to detecting that the eye is properly aligned, automatically instructing the capture of an image of the retina of the properly aligned eye from the imaging device and receiving the image.

20. The computer program product of claim 19, wherein the information indicates that the eye is improperly aligned at the first time due to at least one of:

a pupil of the eye is not shown in the infrared stream; and the imaging device is not focused.

\* \* \* \* \*